(12) United States Patent
Moore et al.

(10) Patent No.: US 8,131,374 B2
(45) Date of Patent: Mar. 6, 2012

(54) ELECTRICAL NERVE STIMULATION DEVICE

(75) Inventors: Gary L. Moore, Cedar, MN (US); John Czech, Bethel, MN (US); Bisrat Woldegiorges, Minnetonka, MN (US); Michael Karas, Edina, MN (US)

(73) Assignee: Encore Medical Asset Corporation, Henderson, NV (US)

( * ) Notice: Subject to any disclaimer, the term of this patent is extended or adjusted under 35 U.S.C. 154(b) by 0 days.

(21) Appl. No.: 13/204,022

(22) Filed: Aug. 5, 2011

(65) Prior Publication Data
US 2011/0288616 A1 Nov. 24, 2011

Related U.S. Application Data

(62) Division of application No. 11/879,221, filed on Jul. 16, 2007, now Pat. No. 8,019,426, which is a division of application No. 10/273,392, filed on Oct. 17, 2002, now Pat. No. 7,254,444.

(60) Provisional application No. 60/330,116, filed on Oct. 17, 2001.

(51) Int. Cl.
*A61N 1/00* (2006.01)
(52) U.S. Cl. ....................................................... 607/46
(58) Field of Classification Search .................. 607/46
See application file for complete search history.

(56) References Cited

U.S. PATENT DOCUMENTS

| | | |
|---|---|---|
| 3,645,267 A | 2/1972 | Hagfors |
| 4,068,669 A | 1/1978 | Niemi |
| 4,088,141 A | 5/1978 | Niemi |
| 4,580,570 A | 4/1986 | Sarrell et al. |
| 4,769,881 A | 9/1988 | Pedigo et al. |
| 5,065,083 A | 11/1991 | Owens |
| 5,146,920 A | 9/1992 | Yuuchi et al. |
| 5,184,617 A | 2/1993 | Harris et al. |
| 5,187,797 A | 2/1993 | Nielsen et al. |
| 5,243,232 A | 9/1993 | Bolda et al. |
| 5,285,781 A | 2/1994 | Brodard |
| 5,312,448 A | 5/1994 | Hognelid et al. |
| 5,755,745 A | 5/1998 | McGraw et al. |
| 5,776,173 A | 7/1998 | Madsen, Jr. et al. |
| 5,836,995 A | 11/1998 | MGraw et al. |
| RE35,987 E | 12/1998 | Harris et al. |
| 5,899,923 A | 5/1999 | Kroll et al. |
| RE36,690 E | 5/2000 | McGraw et al. |
| 6,157,164 A | 12/2000 | Jaworski et al. |
| 6,226,552 B1 | 5/2001 | Staunton et al. |
| 6,292,692 B1 | 9/2001 | Skelton et al. |
| 6,594,527 B2 | 7/2003 | Mo |
| 7,254,444 B2 | 8/2007 | Moore et al. |
| 2003/0120183 A1* | 6/2003 | Simmons ...................... 600/595 |

OTHER PUBLICATIONS

Amrex-Zetron, Inc. AdvanTeq 2000®, Internet printout, 3 pages.

* cited by examiner

*Primary Examiner* — George Manuel
(74) *Attorney, Agent, or Firm* — Ropes & Gray LLP

(57) ABSTRACT

The electrical nerve stimulation unit in accordance with the present invention generally includes a housing, an input panel, a display panel, a controller, a first channel output, a second channel output, and a power system. While the device is generally described in terms of use as a TENS unit, it must be noted that other nerve stimulation applications for the device are envisioned as well. The myriad of intelligent and proactive programmable software functions and features of the present invention are executed on the controller's microprocessor. For instance, open lead monitoring, soft recovery implementation, compliance monitoring, and enhanced power management are all controlled and monitored through the interfacing of the processor with the various devices and hardware on the unit's hardware platform.

16 Claims, 15 Drawing Sheets

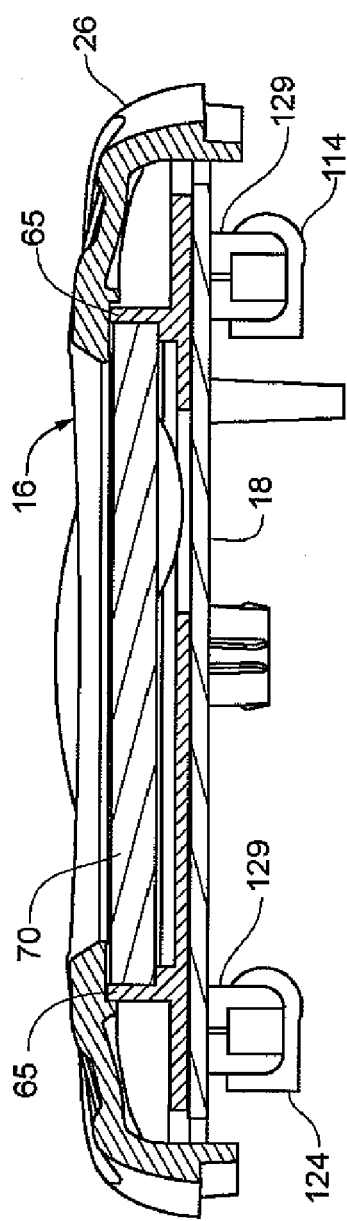
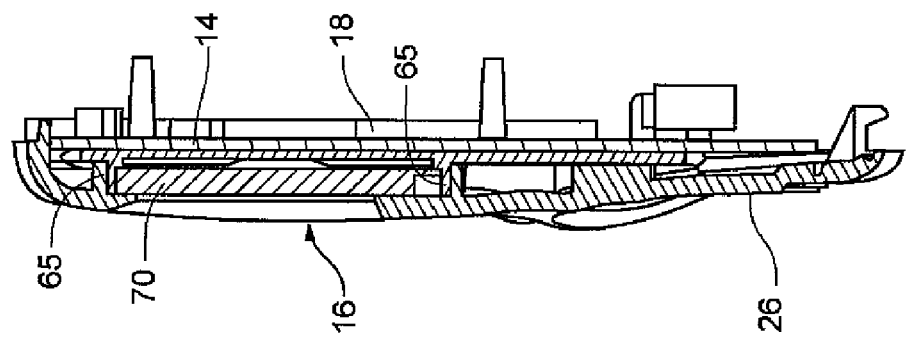

ELECTRICAL NERVE STIMULATION DEVICE

RELATED APPLICATIONS

This application is a divisional of U.S. patent application Ser. No. 11/879,221, filed Jul. 16, 2007, now U.S. Pat. No. 8,019,426, which is a divisional of U.S. patent application Ser. No. 10/273,392, filed on Oct. 17, 2002, now U.S. Pat. No. 7,254,444, which claims the benefit of U.S. Provisional application Ser. No. 60/330,116, filed Oct. 17, 2001. The contents of each of these applications are hereby incorporated herein by reference in their entirety.

FIELD OF THE INVENTION

The invention generally relates to electrotherapy devices used to stimulate the human body. More particularly, the present invention includes improved systems and methods for transcutaneous electrical nerve stimulation (TENS) including compliance monitoring, soft recovery operations, and software controlled power management.

BACKGROUND OF THE INVENTION

Clinical electrotherapy devices are used to implement many different types of human medical therapy protocols. Electrotherapy devices may be used to stimulate nerves in the human body to a large number of therapeutic ends. In addition, electrical impulses cause muscles to contract and may be used for various forms of exercise and pain management.

TENS and microcurrent electrotherapy stimulation have been used successfully for the symptomatic relief and management of chronic intractable pain for many years. In general, TENS or micro current electrical nerve stimulation controls pain of peripheral origin by providing a counter stimulation that interferes with the painful sensations. While the mechanism of action of TENS is not fully understood, there are several theories as to how TENS helps to relieve pain. At the simplest level, stimulating peripheral nerves produces pleasant sensations that assist in distracting the patient from the pain sensation. This distraction is far from trivial and is often advanced as a universal method of pain relief focusing on both the conscious level and subconscious level.

One theory argues that the relief from pain is at least partly based on the knowledge that nerve transmissions carried by large nerve fibers travel more quickly than nerve transmissions carried by small nerve fibers. Under this theory, the electrical stimulations to large nerve fibers created by the TENS unit travel to the brain more quickly, and are more powerful, than pain impulses carried by smaller nerve fibers. Thus, the electrical impulses arrive at the brain sooner than the pain nerve impulses and the sensation of the large nerves overrides and blocks out the sensations from the smaller pain nerves.

Melzack and Walls proposed a working hypothesis of how TENS interferes with pain in 1965. Melzack and Walls proposed that TENS generates an artificial abnormal noise on the nerves to enervate the skin that shares the same nerve roots with the pain fibers conducting the real pain impulses. When the spinal cord receives the barrage of signals from the same region of the body, a neurological circuit turns off and stops relaying the pain impulses to the brain.

Another theory as to the mechanism of action of TENS is based on the understanding that serotonin and other chemical neurotransmitters participate in the pain and the pain reduction process. Under this theory, the electrical nerve stimulation caused by the TENS unit encourages the production of endorphins which then modulate the pain response. Alternately, the electrical stimulations in some way interfere with the production of serotonin which is involved in the pain response.

As a result of the increased understanding and studies surrounding the use of TENS in eliminating or minimizing patient pain, many attempts have been made to more efficiently and effectively implement TENS units. Compliance monitoring, power management, safety and comfort maximization, simplified unit designs, and a myriad of other techniques and methods have been advanced and modified with this increased use of TENS in mind.

Patient compliance with treatment is a medical concern regardless of the form of treatment being applied. Compliance refers to whether the patient is following through with the treatment as prescribed, whether the patient may be avoiding the treatment all together, or whether the patient is in some way applying the treatment in a manner that is not in a form the doctor prescribed and desired. If patients are non-compliant, it becomes very difficult to determine the effectiveness of treatment, as patients are often unwilling to admit they are non-compliant. In addition, some forms of electrotherapy treatment may cause discomfort in which case the patient may have a motivation to avoid the treatment despite its therapeutic benefit. Even further, non-compliance concerns can limit the potential for this treatment technique since misuse will likely weaken the economic and therapeutic draw for health care providers and insurance companies.

As a result of this necessity to implement a level of compliance, some current electrotherapy devices include compliance monitoring protocols. Generally, conventional compliance monitoring protocols include some means of recording the length of time for which the electrotherapy device has been utilized in the period since the doctor has prescribed its use. Conventional compliance monitors only record when the unit is on or off during a given time period. This leaves open the possibility of erroneously monitoring non-compliant use, since the patient may turn on the unit while it is not being utilized for therapeutic use, or the unit may be improperly connected during the power-on period. With regard to improper connections of the unit to the patient, the unit can mistakenly acknowledge therapeutic use during a period of use having no beneficial therapeutic effects on the patient. This leads to great uncertainty as to the effectiveness of the prescribed therapy, whether the current level of treatment is appropriate, or if it is in need of adjustment or discontinuation. Since electrotherapy is generally applied in non-constant electrical pulses, compliance monitoring becomes even more difficult. In general, the present art makes it necessary to maintain voltage during the periods of time in which electrical pulses are not being applied to the patient.

In the past, some compliance monitors have utilized transformers as part of the compliance monitoring circuitry in order to maintain voltage between timing impulses. Due to the physical electrical characteristics of transformers, they are difficult to miniaturize. This contributes to bulkier electrotherapy units. The preferred mode for the application of electrotherapy treatment is one where the treatment can be applied for extended periods of time. This protocol is most easily applied with a unit that can be worn on the body. This allows the treatment to be applied over a long period of time while the patient is involved in normal daily activities. If a unit is to be worn on the body for an extended period of time, a smaller unit is much preferred.

As stated, power management is an important hurdle to overcome in providing effective TENS treatment. The use of portable units capable of attachment to the human body requires battery operation. To promote treatment efficacy and to lower treatment costs, it is necessary to keep the TENS unit circuitry properly powered throughout the duration of the treatment, and to ensure that the patient or health care professionals will not need to replace batteries frequently, or at inopportune times. Conventional techniques to address such power management concerns have left room for measurable improvement. For instance, one technique has been to monitor the voltage level at the battery and to initiate a resulting warning system, such as an LED flash or display panel notification, upon determination by the device that the power has reached a point somewhere below a desired threshold. This system is obviously flawed since it fails to in any way conserve power, or modify performance in an attempt to lengthen the usable life of the battery source, and the resulting treatment period.

Another technique has been to monitor battery power for TENS units by setting a predefined ideal power level, frequently monitoring the overall power level, and making adjustments to power usage once the overall power level of the battery source has reached a level below the ideal power level. While this method does accommodate for lower power, it does so too late, using a power conservation plan that may prove to diminish treatment efficacy. First, power conservation and management is not approached until power has reached a dangerously low level. Second, this critical period of low battery power is dealt with by reducing output power for the TENS unit, which can be obviously undesirable if it negatively effects the proper therapeutic functioning of the unit on the patient.

Conventional attempts at controlling the output signal of the TENS unit to patients following disruptions, defective operations, or operator misuse have also proven problematic as they often fail to properly protect the patient, and the unit itself, from resulting surges. This surge phenomena often occurs when a lead connecting the TENS probe to the patient is disconnected from the main unit and reconnected while the patient is using the device. The natural reaction of the user or patient is to simply reconnect the lead and resume treatment. However, reconnection of the lead can result in a significant jump in power output—from zero to the treatment level. This jump in output signal is virtually instantaneous. As a result, such a quick spike or disruption can damage the unit and, more importantly, cause discomfort to, or even injure, the patient.

One attempt at dealing with the potential harm brought about by these disruptions, has been to provide for monitoring circuitry and/or software within the TENS unit to quickly detect the occurrence of such a disruption. Once the disruption has been detected, the unit quickly ramps down the output signal to approximately zero. At this point of reset, some units will await power approval and adjustment by the user/patient before treatment and power output will be resumed at defined levels. Other prior art teaches immediately ramping up the output signal to pre-disruption levels. Each of these approaches, while an improvement, can be improved upon.

Conventional approaches are directed to accommodation and output signal modification only after a surge has been detected. As a result, the patient and the TENS unit experience at least a momentary spike in the output signal, i.e., a surge upon reconnect of a disengaged lead to the unit. While continuous power surging is not permitted, it is still possible that the patient will be subjected to a period of physical discomfort.

Consequently, there is a need for a TENS unit that substantially overcomes the deficiencies and problems innately present with conventional systems and methods for compliance monitoring, power management, and disruption recovery, and the like.

SUMMARY OF THE INVENTION

The present invention substantially solves the problems with conventional devices by providing a portable TENS unit capable of monitoring true treatment compliance, employing a system of power management that significantly extends the usable life of the battery source, and that implements a soft recovery system that substantially eliminates potential damage to the patient or the unit in those circumstances when an output signal disruption occurs.

The electrical nerve stimulation unit in accordance with the present invention generally includes a housing, an input panel, a display panel, a controller, a first channel output, a second channel output, and a power system. While the device is generally described in terms of use as a TENS unit, it must be noted that other nerve stimulation applications for the device are envisioned as well. The myriad of intelligent and proactive programmable software functions and features of the present invention are executed on the controller's microprocessor. For instance, open lead monitoring, soft recovery implementation, compliance monitoring, and enhanced power management are all controlled and monitored through the interfacing of the processor with the various devices and hardware on the unit's hardware platform.

The present invention includes a compliance monitoring system for use with miniaturized TENS units that is microprocessor controlled such that it is less bulky than transformer-based compliance monitoring systems known in the prior art. The compliance monitoring system includes parameter storage that can provide a mechanism for storing a plurality of non-volatile parameters, including modality, mode, rate, width, cycle, span and timer values. The compliance managing is preferably stored in non-volatile memory, such as EEPROM registers. The memory interfaces with the processor and saves parameters and data while the device is powered off. The processor and software also provide for safety features for setting the intensity to zero when the device is powered on and for providing a self-diagnostic mechanism. This self-diagnostic mechanism is preferably software driven to confirm non-volatile parameter registration validation. The self-diagnostic operation insures that the parameters are stored in the non-volatile memory appropriately. Any corrupted storage of the parameters results in preprogrammed power on default settings, or the statement "service required" can then appear on a display panel.

Several software features interact with the compliance monitoring mechanism:

A lead monitoring feature of the device provides for monitoring of the continuity of at least one active channel lead at the patient pads. The processor provides the open lead status for each channel while that channel is actively delivering a pulse, provided the intensity of pulse delivery is above a minimum threshold level. This lead monitoring function enables the unique soft recovery and compliance monitoring systems of the present invention.

The leads are sampled at selected intervals for each pulse. The software monitors the leads for a feedback pulse within moments, i.e., 4 microseconds, of generating the pulse. This information is stored in the processor. When the software of the processor detects a series of missing pulses, the output shuts down and the display panel displays an open lead condition. By sampling each pulse this way the unit can run in a burst mode without being shut down by the compliance monitoring feature. In burst mode a burst of pulses is followed by a delay before the next burst of pulses. This protocol prevents the unit from showing an open lead condition and shutting down as a result of the burst mode delay.

The software of the processor contains a main program polling function that tracks the input condition of the lead monitor input. Under normal operating conditions the device is actively producing pulses, above a detection threshold, into a set of leads with good contact with the patient's skin. A myriad of possible events can cause these operating conditions to deviate from normal. For example, an electrode may lose electrical connection with the patient's skin, or a lead may lose electrical contact with an electrode. If the operating conditions deviate from the norm, it is possible for the software to take various actions. First, it can immediately reduce the output amplitude on one or both channels to approximately zero milliamps. The second action can be to cause the display panel to read an open channel in place of the normal intensity display. The third action can be to start a 30 second count down clock for powering the unit off. The fourth action can cause the initiation of a polling pulse to look for a reconnected lead. If the lead is reconnected, the software stops the power down sequence. This will then start soft recovery monitoring through software commands at the processor.

The present invention further includes a soft recovery system designed to initiate a software routine at the processor that prevents patients from being startled or injured when current flow at the at least one treatment channel, or both channels, is resumed to the output level previously set by the user/patient following a treatment disruption. Treatment disruptions can include lead disengagement at the electrical stimulation unit, electrode disengagement from the treatment site, manual user mode changes, and the like. The soft recovery system constantly monitors for an open lead condition. If such a condition is detected, the output intensity to the at least one treatment probe is set to approximately zero, or a relatively negligible value of 8 milliamps or less. Once the open lead condition is replaced with a closed lead condition (i.e., the TENS unit lead is reconnected), the microprocessor begins a ramp up stage wherein the output intensity level is incrementally increased over a predetermined time interval to eliminate the problematic surge conditions that plague conventional units.

Power management is implemented into the high voltage circuit to preserve battery energy by software control performed by the processor. The software reads the programmed set output and accordingly drives the high voltage circuit to a target voltage level to obtain the set output. Conventional high voltage circuits are set at a fixed voltage to get the maximum available output that can be delivered. As such, the maximum voltage setting is maintained even when an output less than the maximum output is required by the user. Such rigid and inconsiderate conventional techniques provide for inefficient power management as they unnecessarily drain energy from the battery source.

The TENS unit of the present invention additionally includes a power shut off feature. Preferably, in situations where the TENS unit of the present invention is in an idle or waiting stage, the unit will initiate a shut down program via the microprocessor. For instance, if an open lead condition is present, and the condition has not been resolved within a predetermine period of time, the software of the unit can immediately initiate shut down to preserve power consumption. This shut down procedure can also be initiated if the unit has waited to no avail for a user input response for a predetermined period of time, if the unit has sat idle in a state of non-use, and under like circumstances. The initiated shut down procedure can be the same as when the unit is shut off manually by the user. Examples of shut down initiators can be when there is an unsolved open lead condition, following a period of no input after power up, and when a low battery condition or set treatment time has elapsed.

BRIEF DESCRIPTION OF THE DRAWINGS

FIG. 5a is a cross-section side view of a front panel and corresponding components for a nerve stimulation device;

FIG. 5b is a cross-section front view of a front panel and corresponding components for a nerve stimulation device;

FIG. 8b is a front view of the surface mountable multi-pin connector of FIG. 8a;

FIG. 8c is a side cross-section view of the surface mountable multi-pin connector of FIG. 8a;

DETAILED DESCRIPTION OF THE INVENTION

Figure 1A:
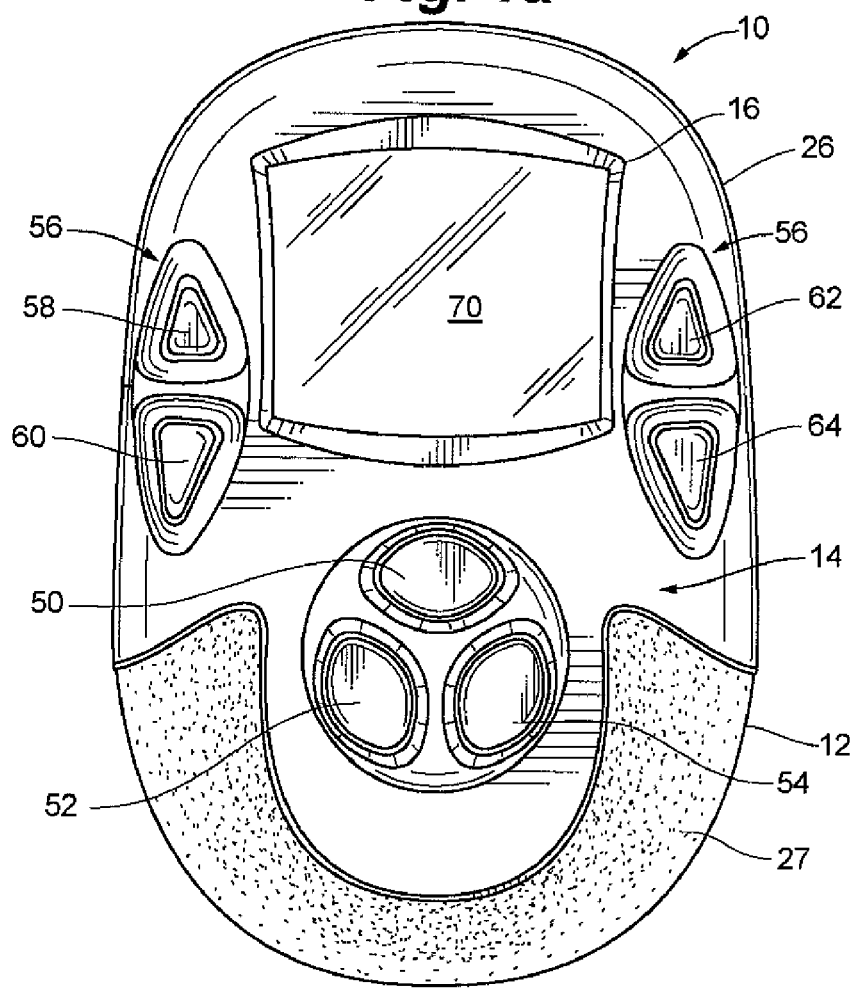
FIG. 1a is a front view of an embodiment of a nerve stimulation device.
Figure 2:
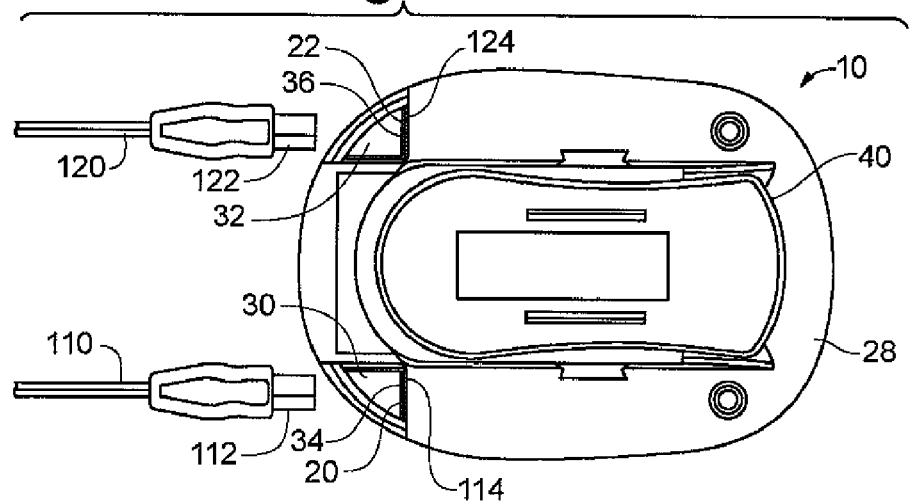
FIG. 2 is a back view of an embodiment of a nerve stimulation device.
Figure 1B:
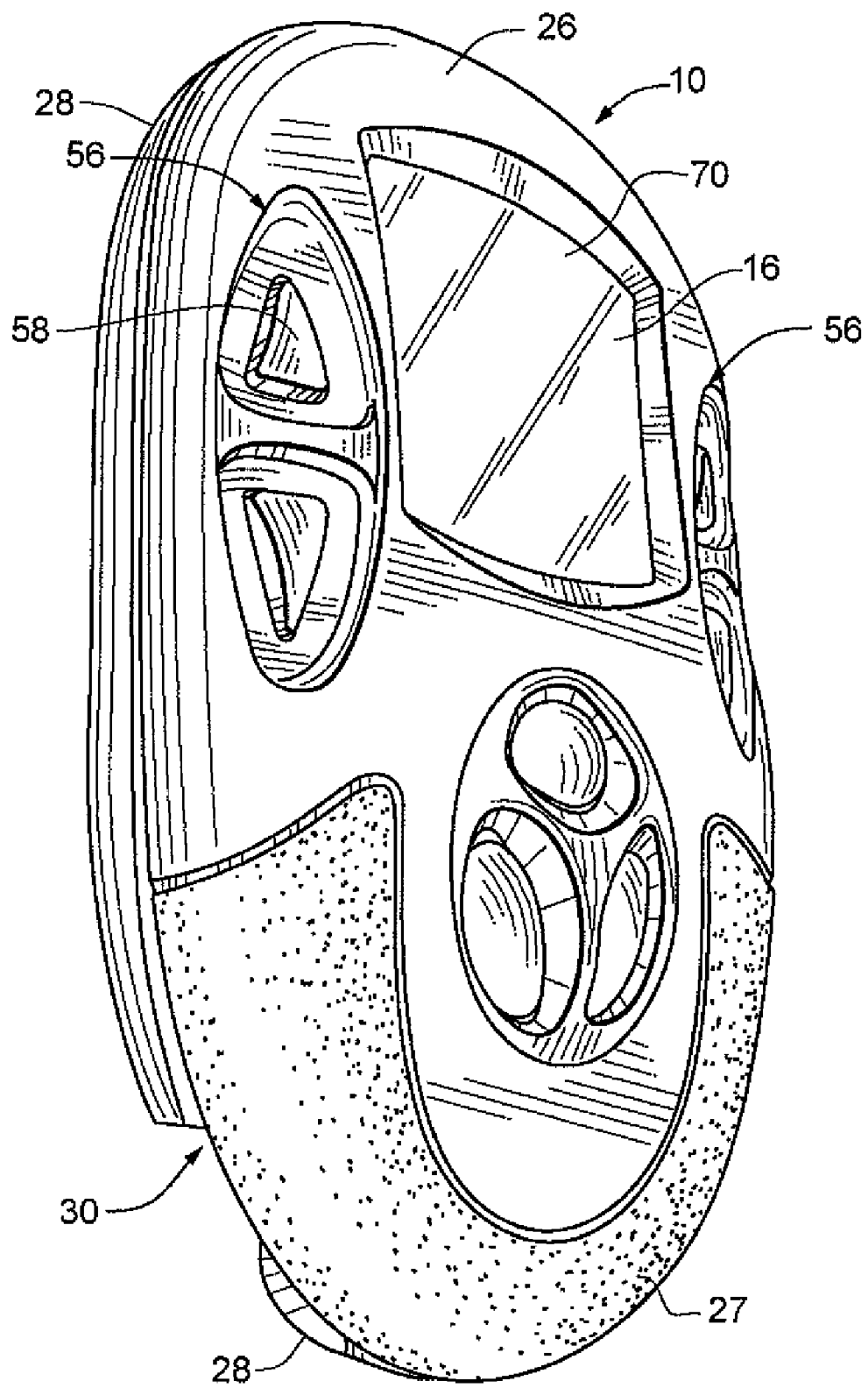
FIG. 1b is a perspective view of an embodiment of a nerve stimulation device.

Referring to FIGS. 1-9e, the electrical nerve stimulation unit 10 in accordance with the present invention generally includes a housing 12, an input panel 14, a display panel 16, a controller 18, a first channel output 20, a second channel output 22, and a power system 24. While the device 10 is generally described in terms of use as a TENS unit, it must be noted that other nerve stimulation applications for the device 10 are envisioned as well.

The housing 12 generally includes a front panel 26, a back panel 28, a clip portion 38, a power access panel 44, and a battery compartment 46. The housing 12 can be of substantially oval shape and have selected components (specifically, the panels 26, 28) preferably constructed of a durable injection molded plastic material such as flame-resistant thermoplastic resins. It will be understood that other materials and shapes can be employed as well.

The front panel 26 includes a section to accept the display panel 16 such that the internally mounted display 16 is visible to a user/patient. Further, the front panel 26 can include a perimeter portion 27 defined by a material change along a boundary of the oval front panel 26. The perimeter portion 27 can be constructed of rubber, plastic, and a myriad of other materials. The back panel 28 includes a first lead recess 30 having a first lead aperture 34, and a second lead recess 32 having a second lead aperture 36. The first and second lead apertures 34, 36 provide connectable communication between attachable lead wires and the internal electronic components of the device 10. The front panel 26 and back panel 28 are shaped and designed for abuttable attachment.

Figure 3:
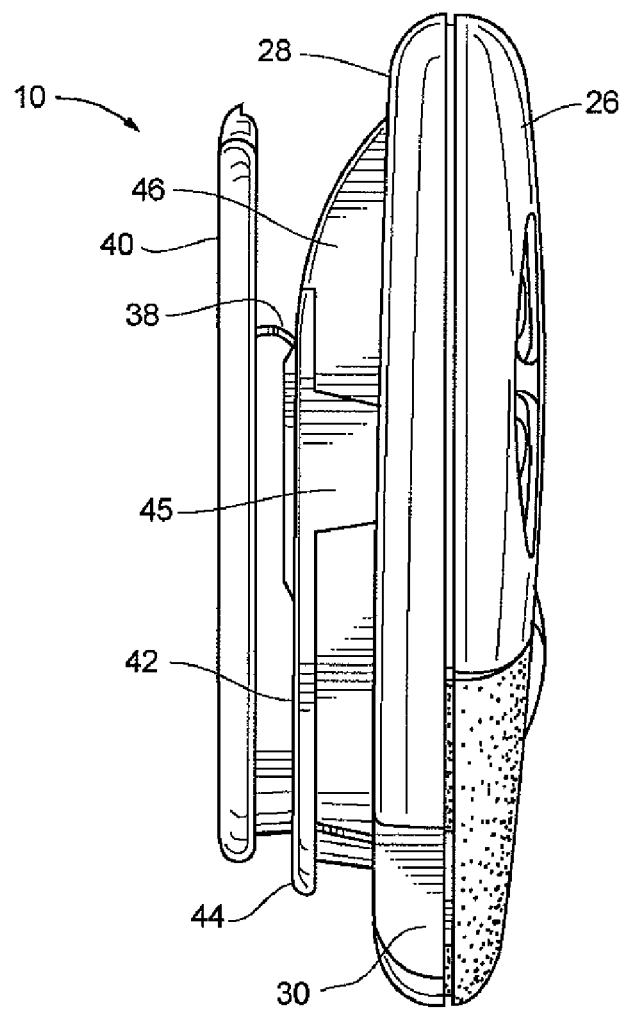
FIG. 3 is a side view of an embodiment of a nerve stimulation device.
Figure 6:
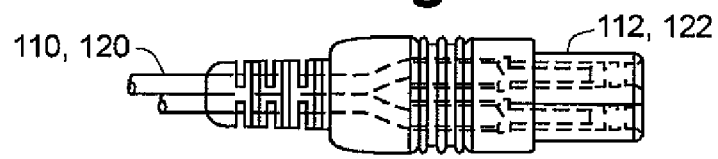
FIG. 6 is a plan elevation view of a lead wire male connector for a nerve stimulation device.
Figure 7:
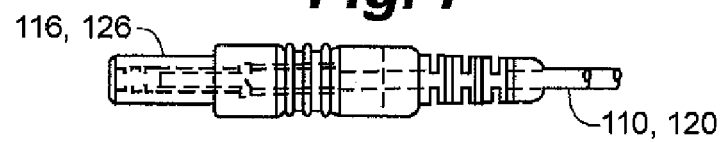
FIG. 7 is a plan elevation view of a lead wire electrode connector for a nerve stimulation device.

The clip portion 38 can include a belt clip 40 and an attachment member 42, as shown in FIG. 3. The clip portion 38 and its corresponding components 40, 42 are selectively fixed to the back panel 28 to promote removable convenient attachment of the device 10 to the user's person. The attachment member 42 is removably attached to the belt clip 40, with the member 42 being connectable to the back panel 28. The attachment member 42 is constructed of a material having spring-like, rebounding characteristics, such as thin metal, wherein measurable pulling force on the belt clip 40 by the user will permit selective attachment of the device to a belt, carrying case, shirt pocket, and other like regions.

The power access panel 44 is generally proximate the clip portion 38 on the back panel 28 of the device 10, as shown in FIG. 3. The power access panel 44 is preferably a door panel providing selective access into the battery compartment 46. In one embodiment, the power access panel 44 includes at least two pressure tabs 45 wherein the panel 44 can be disengaged from its locked position by applying measurable pressure on the tabs 45. Other removably lockable devices known to one skilled in the art can be employed as well. The battery compartment 46 is sized and shaped for operably receiving at least one battery source 48. In one embodiment, the at least one battery source 48 is a plurality of standard or rechargeable AAA batteries, wherein each individual battery is capable of holding a 1.5 volt charge. In addition, power packs, a 9 volt battery, and other known battery sources can be utilized without deviating from the spirit and scope of the present invention.

Figure 4A:
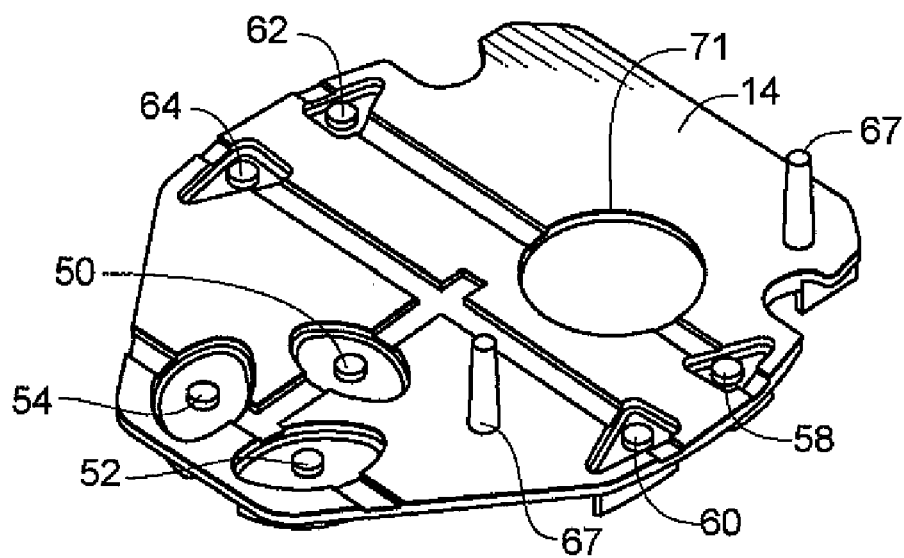
FIG. 4a is a perspective back view of a flexible keypad for a nerve stimulation device.
Figure 4B:
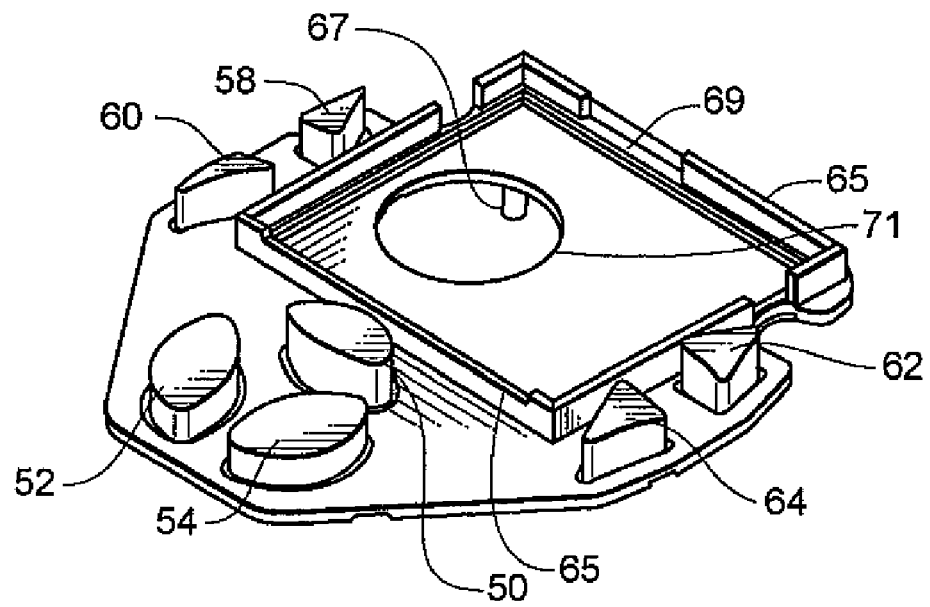
FIG. 4b is a perspective top view of a flexible keypad for a nerve stimulation device.
Figure 8A:
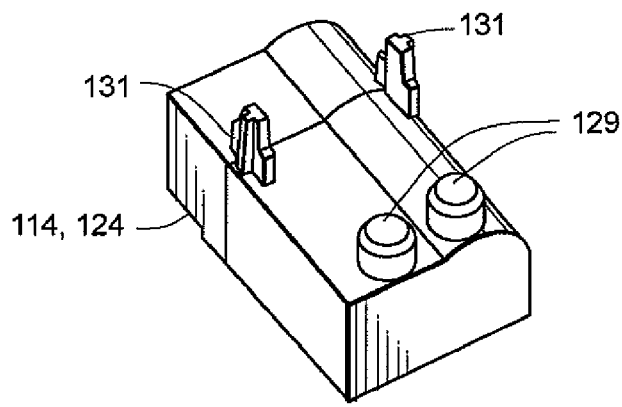
FIG. 8a is a perspective view of a surface mountable multi-pin connector for a nerve stimulation device.
Figure 8B:
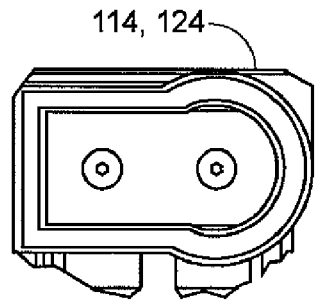
Figure 8C:
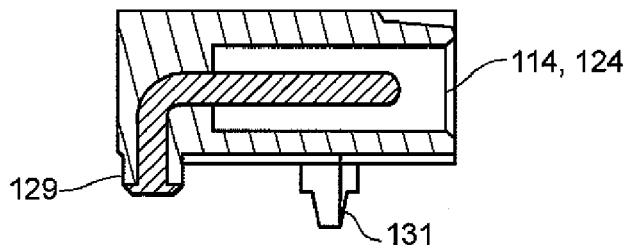
Figure 8D:
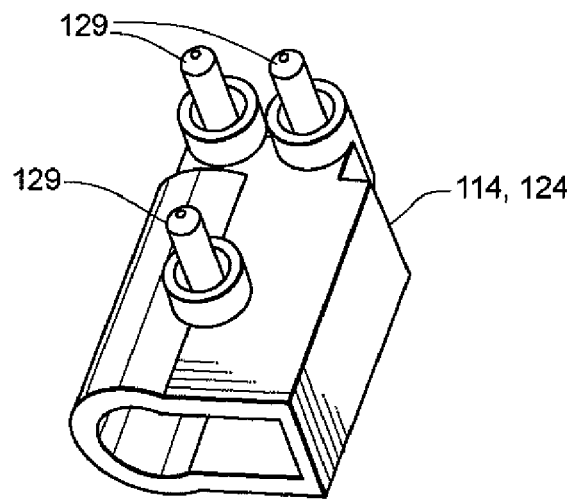
FIG. 8d is a perspective view of a multi-pin connector for a nerve stimulation device.
Figure 8E:
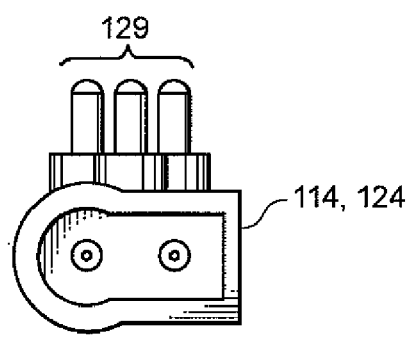
FIG. 8e is a front view of the multi-pin connector of FIG. 8d.

The input panel 14 preferably comprises a plurality of input keys defined on a user input keypad. Referring primarily to FIG. 1*a*, and FIGS. 4*a*-4*b*, the plurality of keys can include a power key 50, a mode selection key 52, a pulse control key 54, and a plurality of channel intensity keys 56. These channel intensity keys 56 include a channel 1 intensity increase key 58, a channel 1 intensity decrease key 60, a channel 2 intensity increase key 62, and a channel 2 intensity decrease key 64. Each of the keys for the input panel 14 are in operable communication with the controller 18 to control various functions and performance characteristics of the device 10, as will be explained herein. Each of the input panel 14 keys are preferably constructed of a silicon rubber with respective push-button control switch functionality. The power key 50 controls power toggling for the device 10 between on and off settings. The channel intensity keys 60-64 permit independent fine-tuning of the intensity output adjustments for each channel 20, 22. The pulse control key 54 enables control of the rate, cycle, pulse duration, and pulse span for applicable treatment sessions. The mode selection key 52 permits the user to select the modality of the desired TENS treatment according to predetermined treatment goals. Preferably, each of the keys 50-64 will be recess seated within the front panel 26 to enhance ease-of-use (i.e., simple key location) and to minimize accidental key engagement.

Figure 9A:
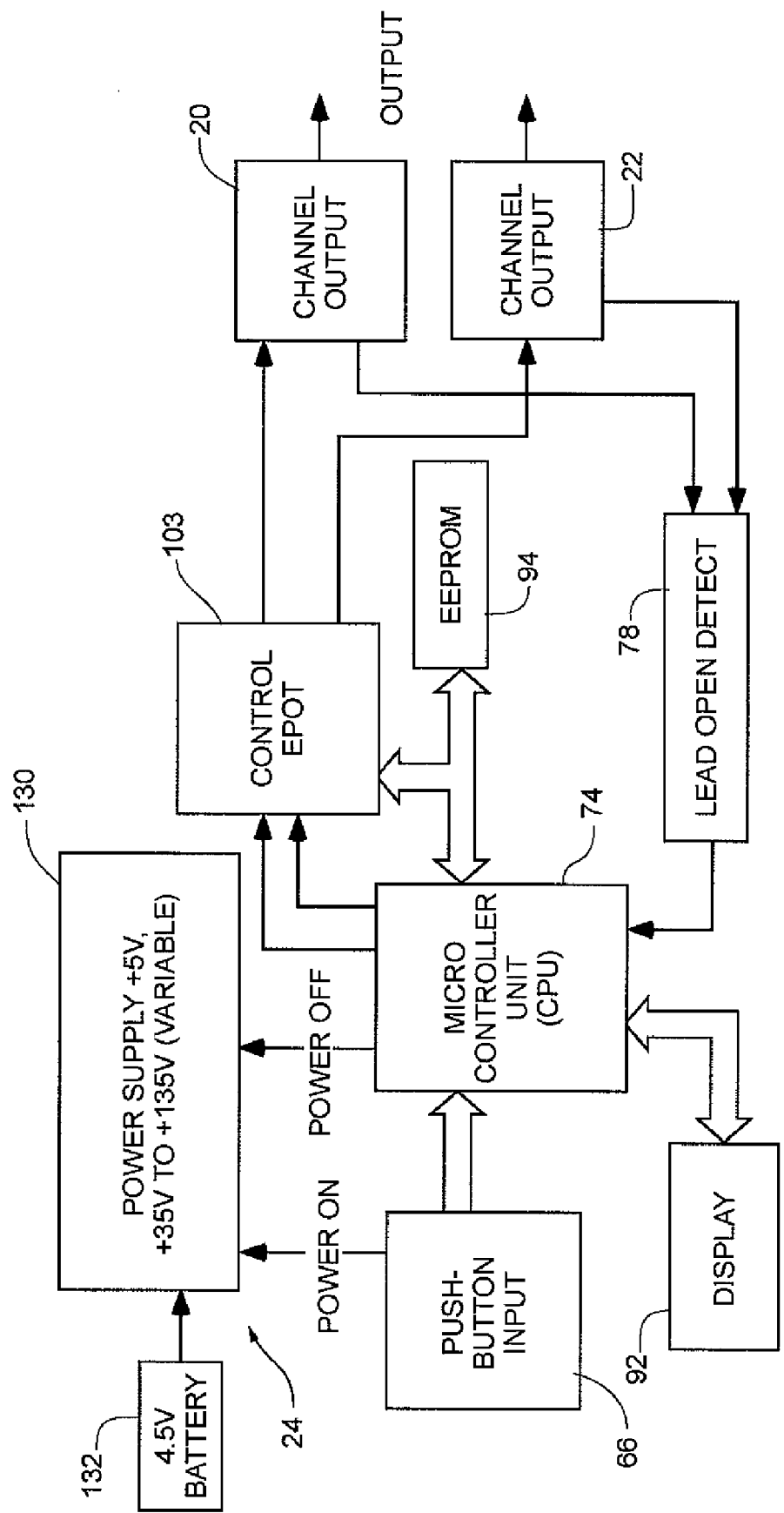
FIG. 9a is a block diagram of a controller and/or components for a nerve stimulation device.
Figure 9B:
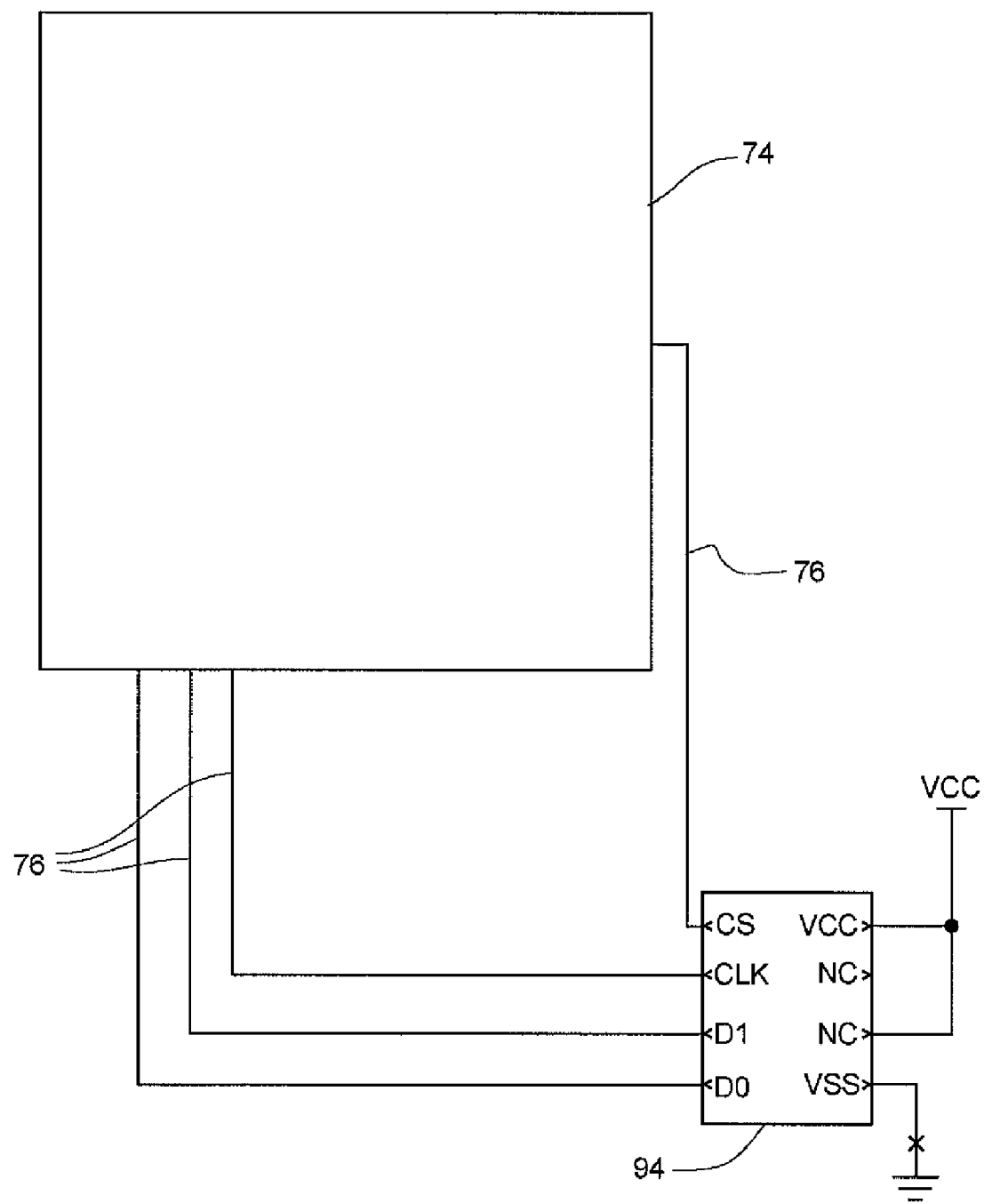
FIG. 9b is a schematic diagram of selected I/O and storage components of a controller for a nerve stimulation device.

The display panel 16 preferably includes a Liquid Crystal Display ("LCD") screen 70, as shown best in FIG. 1*a*, and FIGS. 5*a*-5*b*. The LCD screen 70 is housed behind the front panel 26 to be visibly located at the upper portion of the front panel 26, as will be discussed herein further. In one embodiment, the LCD screen 70 is a four line display having eight characters per line, with each display character being composed of a matrix of display dots laid out five horizontally and eight vertically. The LCD screen 70 can display alpha numeric characters, such as those understood under ASCII standards. Output parameters and prompting for user input are displayable on the LCD screen 70. An LCD controller 92 operably interfaces the LCD screen 70 to the controller 18 to provide direct line access and data communication therebetween, as shown in FIG. 9*g*.

In one embodiment, as shown in FIGS. 4*a*-4*b*, the input panel 14 is a flexible pad or gasket-like structure being operably positionable between the abuttable front and back panels 26, 28. Namely, the input panel 14 is operably attachable to the controller 18 hardware platform of the device 10 on one side and sized and positioned for engagement of the keys 50-56 on the opposite pad side upon alignment with the front panel 26 key recesses. In such an embodiment, the flexible input panel 14 can be made of a flexible polymer, with specified portions typically being combined, injected, or extruded with a conductive material such as carbon. In addition to the integrated keys listed herein, the flexible input panel 14 generally includes a LCD frame nest portion 65, at least one seating post 67, and a seating aperture 71. The LCD frame portion 65 can include a ribbon cable 69. The LCD frame portion 65 is sized and shaped to securably receive the LCD panel 70 such that the LCD panel 70 is provided a resting place prior to alignment and abuttable attachment of the front panel 26 to the back panel 28. The ribbon cable 69 permits access by a data ribbon into the seated LCD 70 through the LCD nest 65 to facilitate communication between the LCD 70 and the controller 18 without interfering with the seating of the LCD 70. The seating posts 67 provide means of engaging a corresponding portion of the controller 18. The seating posts 67 are positioned such that they will provide for a consistent and properly aligned keypad 14 wherein connectable alignment of the posts 67 to the controller 18 results in proper alignment of the keys 50-56 to a corresponding at least one key switch 66. As a result, pressing of the keys 50-56 will result in an engagement with the key switches 66 which will be processed by the processor 74 of the controller 18.

Each of the keys 50-64 are in operable communication with a key switch 66 that can consist of output lines and input lines to the controller 18. Software monitoring of the key switch 66 for each key is performed such that control registers serve to identify the keys and their corresponding activity. These register identities result in a control matrix to determine the current key, and the key depression status.

Referring specifically to FIGS. 9a-9e, the controller 18 includes at least a processor 74, at least one open lead detect circuit 78, the LCD controller 92, non-volatile memory 94, and a communication port 98. In addition, waveform generator control circuitry can be included in operable communication with the processor 74. The processor 74 in one embodiment can further comprise input/output ("I/O") controls 76 that provide dedicated and selectively controllable data communication lines to each of the hardware devices and circuitry within the TENS unit 10. These I/O controls can include a display line, an input panel line, a power supply line, an oscillator line, a waveform generator line, a first channel monitoring line, and a second channel monitoring line. The processor 74 can communicate with, control, and process data from each of the interfaced controls 76.

The non-volatile memory 94 (FIG. 9b), such as EEPROM, can be erased and reprogrammed using special software access procedures. The non-volatile memory 94 can be employed to store previous operating parameters, error flags, critical operating parameters, device defaults, configuration flags, and a myriad of other data which is desirously maintained while the device 10 is powered off. The memory 94 can be selectively programmed and reprogrammed using the communication port 98, as shown in FIG. 9f. In one embodiment, the communication port 98 is a serial data port for receiving an external device to perform reprogramming, testing, and like operations. Other data communication interfaces known to one skilled in the art are also envisioned for use with the present invention. For instance, at least one test contact point 99 can be included to provide for jumper type contact of a device for downloading and uploading communication with the controller 18, and the non-volatile memory 94 in particular.

In one embodiment, the processor 74 includes at least 32 Kilobytes of flash memory for software storage and reprogramming, and 512 bytes of RAM for a stack and to provide storage for operating parameters and variables. Other processor 74 embodiments equipped with varying configurations, such flash memory and RAM, are envisioned for use with the present invention as well. As will be further explained herein, the processor 74 and its reprogrammable software enables focused control over the operation of the hardware/circuitry platform for the device 10, as well as specific control, monitoring, and data processing for the specific short-term and long-term treatment.

In one embodiment, the waveform generator control circuitry includes a first channel output circuit, and a second channel output circuit, with each output circuit corresponding to an output channel 20, 22, respectively. The output waveforms generated are typically square waves. The processor 74 interfaces with the output circuits and provides programmed intensity, pulse rate, and pulse width signals. Preferably, the output signals to each channel 20, 22 is driven such that the two pulses are positioned 180 degrees out of phase with respect to the other channel. The oscillator of the processor 74 controls the timing of the two pulses. In one embodiment, the waveform generator control circuitry will include an EPOT chip 103 that will provide a programmable resistor divider allocation in 256 equal steps on each channel 20, 22 to control the pulse amplitude, as shown in FIGS. 9a and 9e. For instance, the EPOT chip 103 can be programmed to designate the pulse amplitude from 0 to 127 milliamperes in 1 mA steps.

Figure 9C:
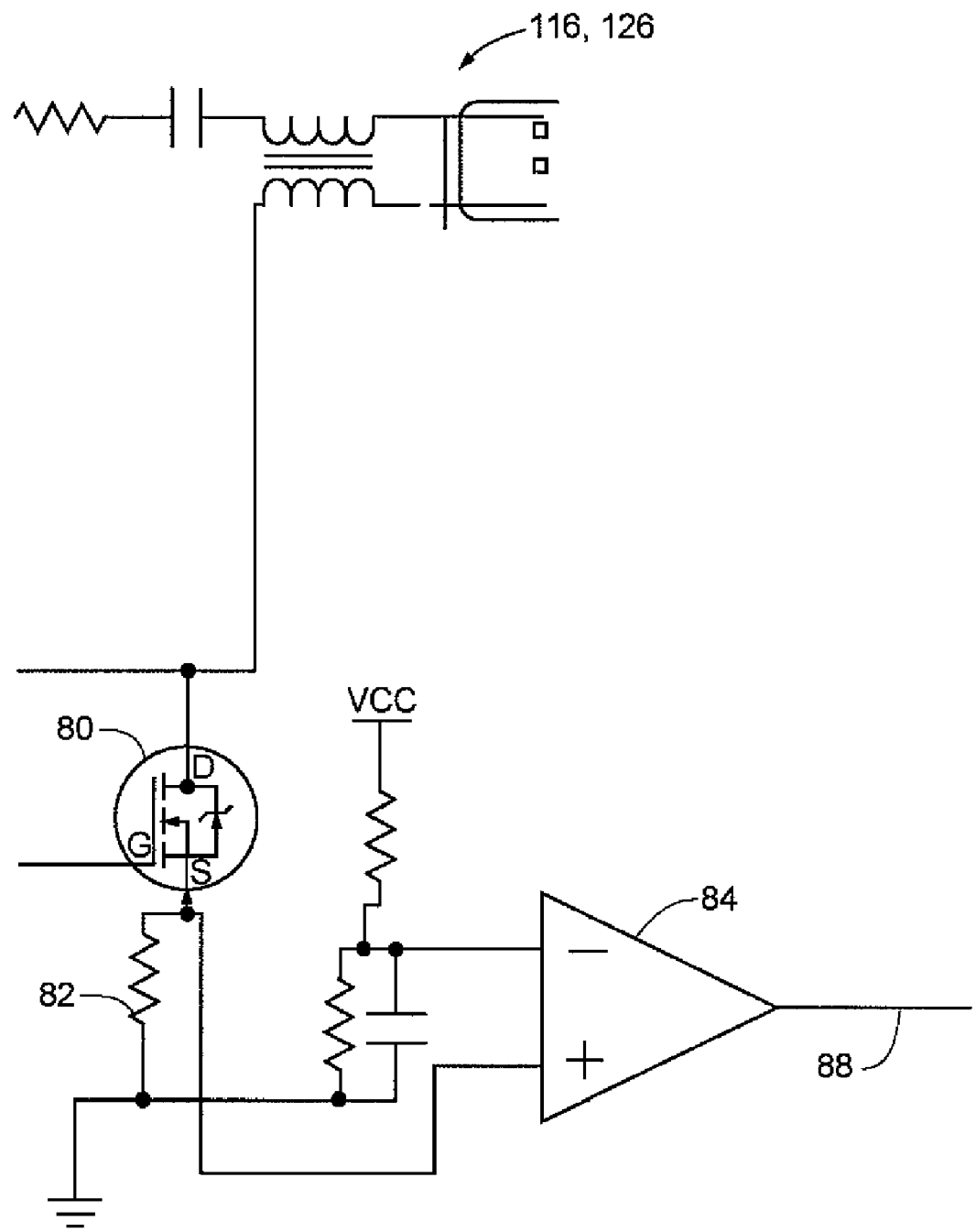
FIG. 9c is a schematic diagram of an open lead monitoring circuit for a nerve stimulation device.

In the embodiment shown in FIG. 9c, the open lead detect circuit 78 includes a transistor 80, a resistor 82, a comparator 84, the electrode connector 116, 126, and an output line 88. The open lead detect circuit 78 depends on the current flow out from the connector 116, 126 through the patient and returnable to the circuit. Upon return of the flow, the current passes through the transistor 80 and then through the resistor 82. This flow through the resistor 82 will generate a voltage which can be used at the "+" input to the comparator 84. When the voltage at the "+" input to the comparator 84 exceeds the reference voltage on the "−" input to the comparator 84, a signal is sent out from the comparator 84 through the output line 88 to the processor 74. It should be noted that this embodiment, or other lead detection circuit embodiments, can be implemented for both channels of the device.

Referring primarily to FIGS. 6-7, and FIGS. 8a-8e, the first channel output 20 includes a first lead wire 110. In one embodiment, the first lead wire 110 has a first lead male connector 112 at one end for removable attachment to a first lead multi-pin connector 114 housed within the device 10 in the back panel 28. The multi-pin connector 114 is recessed relative to the overlapping front panel 26 such that a portion of the male connector 112 is covered and protected by the front panel 26 to form a recessed jack when engaged. In addition, a first lead electrode connector 116 is included at the end of the first lead wire distal the first male connector 112. A treatment electrode is designed for removable attachment to the first lead electrode connector 116 to receive treatment pulses from the lead wire 110 of first channel output 20. The recessed jack feature is clearly demonstrated in FIGS. 1b and 2.

Similarly, the second channel output 22 includes a second lead wire 120. In one embodiment, the second lead wire 120 has a second lead male connector 122 at one end for removable attachment to a second lead multi-pin connector 124 housed within the device 10 in the back panel 28. The multi-pin connector 124 is recessed relative to the overlapping front panel 26 such that a portion of the second lead male connector 122 is covered and protected by the front panel 26 to form a recessed jack when engaged. In addition, a second lead electrode connector 126 is included at the end of the second lead wire 120 distal the second lead male connector 122. A treatment electrode is designed for removable attachment to the second lead electrode connector 126 to receive treatment pulses from the lead wire 120 of second channel output 22.

In one embodiment, the connectors 114, 124 can be surface-mounted to the controller 18, i.e., a circuit board, wherein at least one member 131 provides the attachment point to the controller 18. In addition, at least one connector line 129 provides communication with the controller 18, and can, in alternative embodiments, provide the attachment point to the controller 18. FIGS. 8a-8e show potential embodiments for the connectors or jacks 114, 124, while FIGS. 8a-8c in particular are directed to surface-mountable connectors 114, 124. Other embodiments with these structural characteristics and features are envisioned for use with the present invention as well. In addition, non-surface-mounted connectors 114, 124 or jacks can also be employed, such as those shown in FIGS. 8d-8e. Regardless, the connectors 114, 124 are securably alignable with the corresponding lead apertures 34, 36 of the lead recesses 30, 32 of the back panel 28 to form the recessed jack for protective engagement of the lead wires 110, 120.

Each of the electrodes provide electrical conduction to the patient's/user's skin based on output pulse signals from the output channels 20, 22. The electrodes are typically constructed of carbon, foil, stainless steel, or other like materials. The electrodes are insulated and can be used with a gel material to provide adhesive contact and even dispersion of electrical energy to skin tissue. It should be noted that various electrodes known to one skilled in the art can be employed for use with the present invention.

Figure 9D:
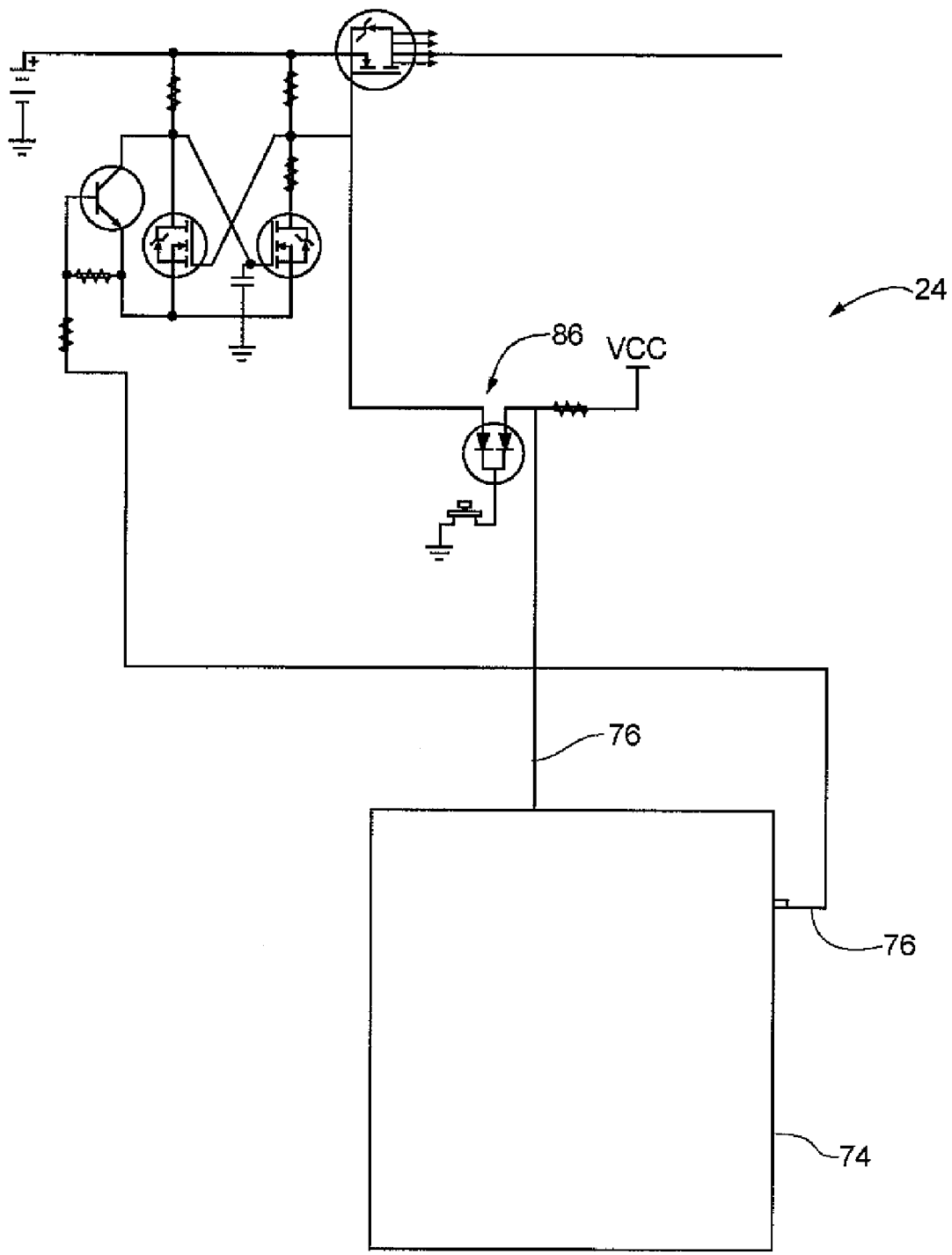
FIG. 9d is a schematic diagram of a power on-off switch control system for a nerve stimulation device.
Figure 9E:
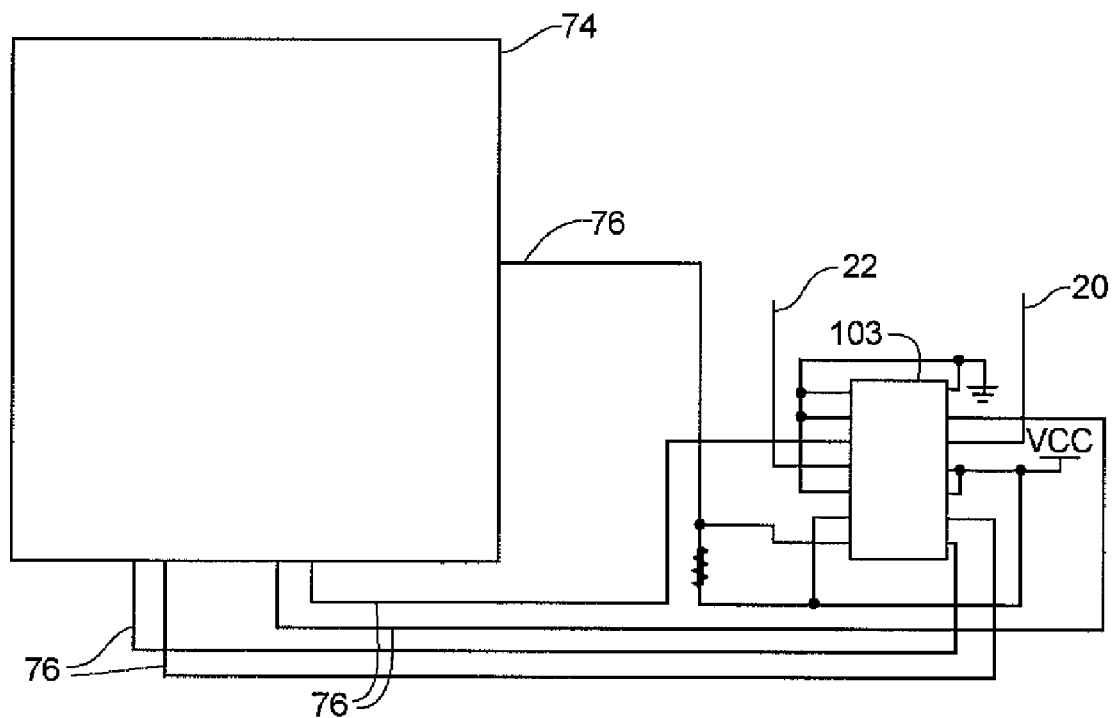
FIG. 9e is a schematic diagram of controller components and pulse control for a nerve stimulation device.
Figure 9F:
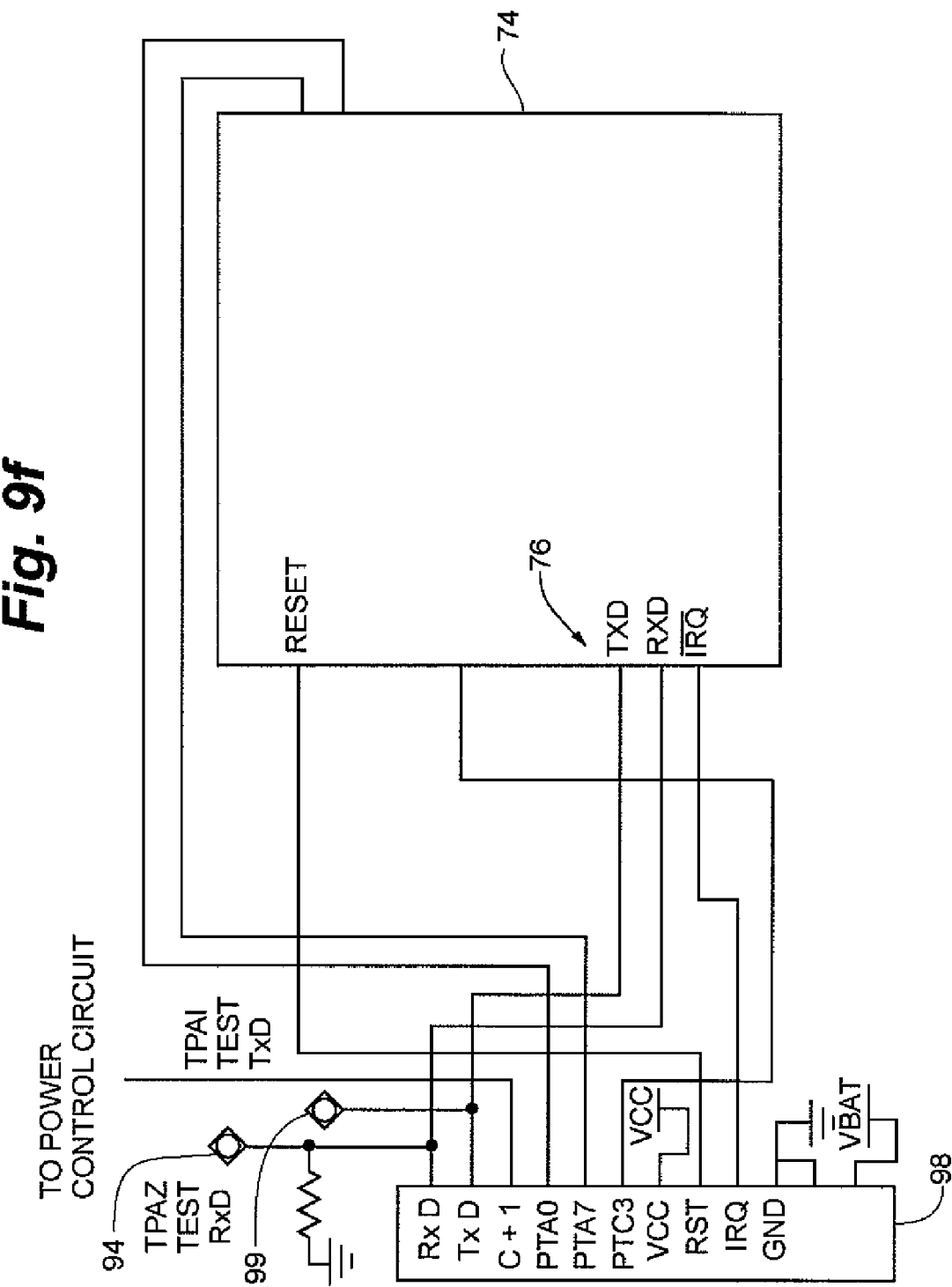
FIG. 9f is a schematic diagram of controller components and a communication port for a nerve stimulation device.
Figure 9G:
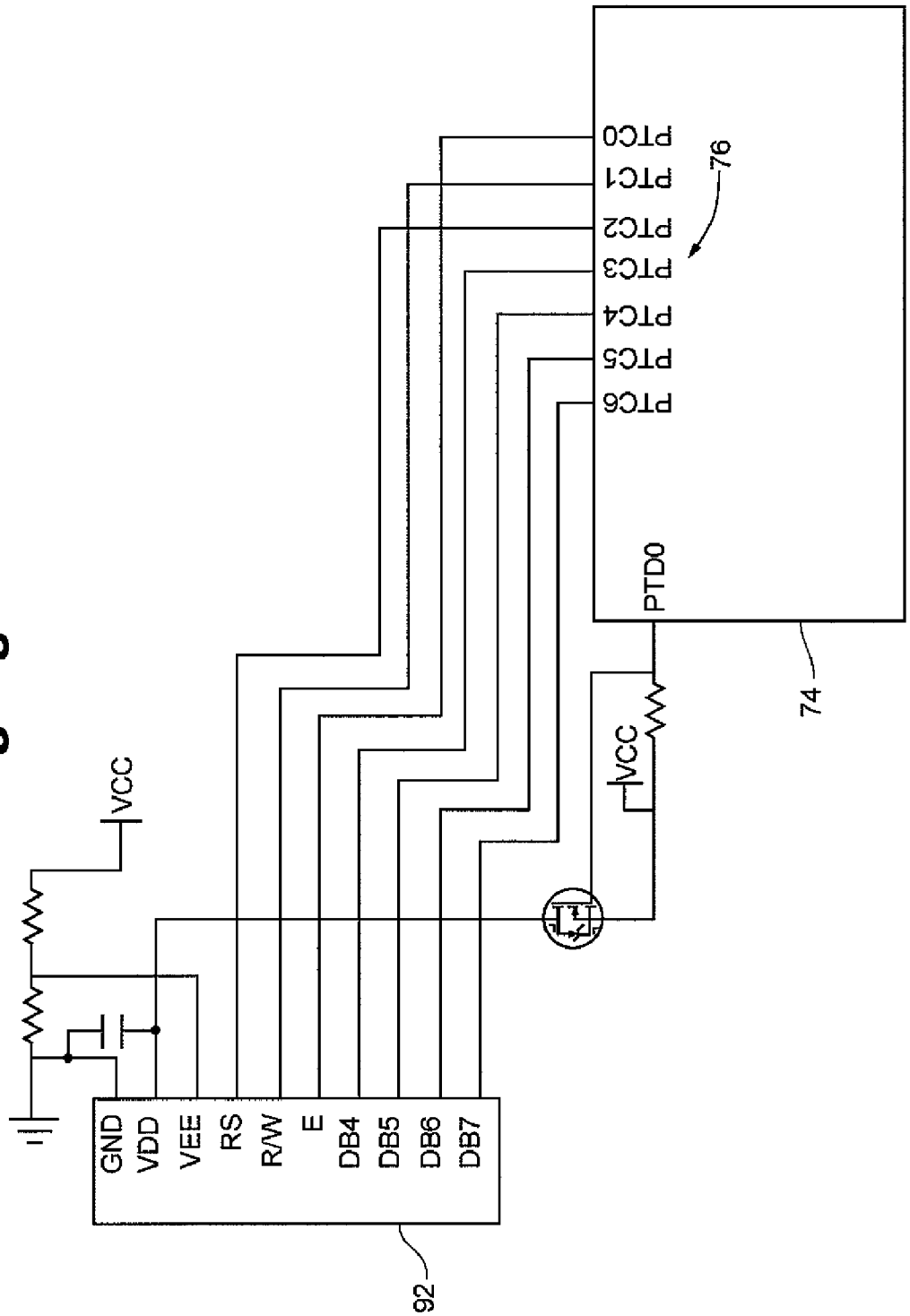
FIG. 9g is a schematic diagram of controller components and a display controller for a nerve stimulation device.

FIG. 9d demonstrates one embodiment of the power system 24 designed for power off procedures at a manual switch 86 or through the control of the processor 74. The power system 24 generally comprises a DC power supply 130 operably connected to a battery power pack 132 for providing power to the hardware platform of the device 10, as shown in FIG. 9a. As stated herein, the power source for the power pack 132, and the device 10, is preferably three AAA 1.5 volt batteries, or a 9.0 volt battery. In one embodiment, the power system 24 is preferably designed to comply with safety standards EN6060101, UL2601, and ANI/AAMI NS4-85 requirements.

In operation, power to the device 10 is accomplished by engaging or pressing the power key 50. As stated, the controller 18 scans the key switch 66 for activation of any of the designated keys 50-64, such as the power key 50. At this power up stage, the processor 74 will retrieve from the non-volatile memory 94 any stored operating parameters. Generally, these operating parameters were stored from the most recent treatment session and will include settings for mode, rate, width, cycle, span, and timer functions. The processor 74 can write to the non-volatile memory 94 through dedicated I/O serial interfaces therebetween. In one embodiment, the power up initiation of the device 10 will prompt the processor 74 reliability algorithms to verify the reliability of the software programs, RAM, ROM, timing, EEPROM, and other hardware and software functions.

The processor 74 will initiate a power down stage upon detecting engagement of the power key 50 during a power on period. At the power down stage, the processor 74 will reduce the intensity of the outputs to the first and second output channels 20, 22 to zero and initiate a shut down sequence. The shut down sequence, under normal circumstances, will include storing the operating treatment parameters such as mode, pulse rate, pulse width, compliance parameters, timing parameters, and the like, to the non-volatile memory 94. As described herein, each manual or processor-initiated power down can include this reference sequence of storage events to the non-volatile memory 94 to preserve the data during power off periods.

In addition, the TENS device 10 can include an automatic shut off function performed by the processor 74. This function will generally trigger upon the occurrence of a timing event in conjunction with a treatment disruption or inactivity. For instance, if the processor 74 detects a lead continuity break, it will initiate a timing sequence. If continuity of the lead is not re-established within the predefined time period, such as 30 seconds, the power down sequence is initiated (i.e., operating parameters are stored and the power is turned off). Other events can also trigger the timing sequence for shut down. For instance, failure to provide user input upon display prompting, disengagement of the electrode from the patient's skin, output inactivity, and a myriad of other considerations and activity can be defined as triggering events by the software of the processor 74.

At power up, the LCD panel 70 can display the default mode assigned by the processor 74 according to the stored operating parameters retrieved from the non-volatile memory 94. There can be a plurality of preprogrammed TENS modes for the device 10. These modes can include normal mode, strength duration mode, SMP mode, burst mode, rate modulated mode, width modulated mode, and multi-modulated mode. By pressably engaging the mode selection key 52, it is possible for the user/patient to toggle between these modes.

To provide for electrical stimulation treatment, parameters for pulse intensity, pulse rate/cycle, and pulse duration/width parameters are set and appropriately adjusted. As will be discussed herein, the appropriate parameters can vary depending on the treatment modes selected by the user. For instance, the intensity can be programmed to default to zero when the device 10 is initially powered on, with the output intensities of the pulses at each channel 20, 22 being independently adjustable in a linear manner from 0% to 100% in steps of 1%. In addition, the output can be expressed in output percentage, milliamps, volts, and the like. Other stepped interval options are also envisioned. These interval adjustments are made at channel intensity keys 58-64.

The operational range of the pulse rate/cycle is typically between 2 and 160 Hz, or pulses per second (PPS). To facilitate therapeutic pain control, also known as endorphin control, the adjustment can generally be made in 2 PPS increments below 20 PPS, and 4 PPS increments above 20 PPS. Upon prompting at the LCD screen 70 for a pulse rate change, keys 58-64 can be utilized for adjustment, wherein the processor 74 directly controls the rate by regulating the time from the beginning of one pulse to the beginning of the next. The pulse width adjustment is controlled at the processor 74 by regulating the time from the beginning of a pulse to the end of that same pulse. Preferably, the pulse width is adjustable in 5 µsec increments over the operational range between 50 µsec and 400 µsec (+/−2 µsec). Other incremental variations are also envisioned for use with the present invention 10.

Figure 10:
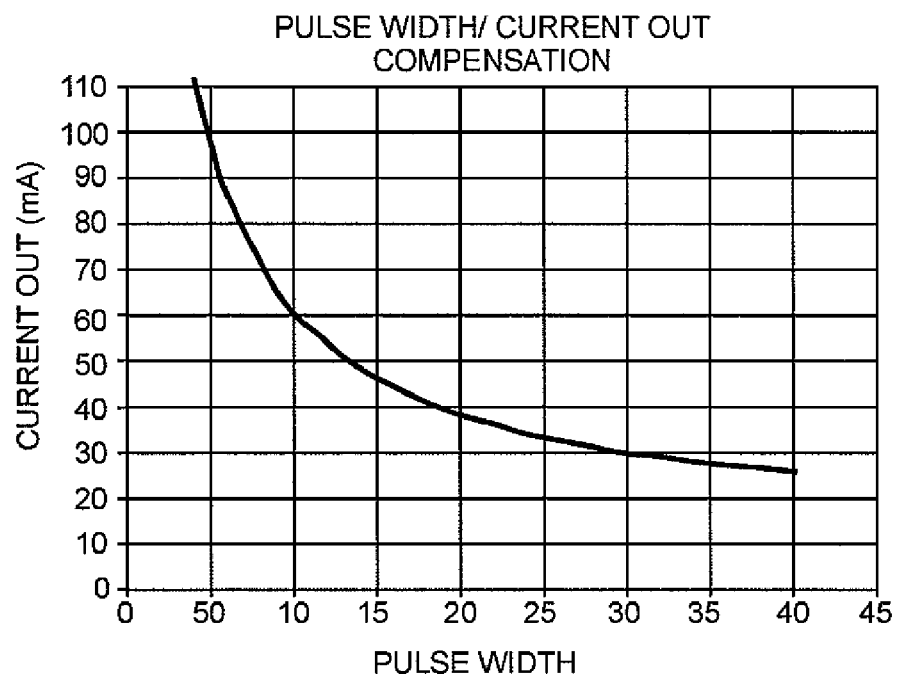
FIG. 10 is a graphical representation of a strength duration curve.

In one embodiment, the present invention 10 provides for an automatic pulse duration/width compensation system that maintains a fixed relationship between the pulse duration and the output amplitude as demonstrated in the strength duration curve of FIG. 10. When the pulse duration changes, the amplitude is adjusted automatically to follow the curve. Preferably, this automatic compensation occurs in normal mode, burst mode, strength duration mode, or in any combination of modes. The strength duration curve describes the required output intensity for a given pulse duration as defined by the following equation:

$$I = 19.6 \cdot A / 1 - e^{-0.0030593(21.338 + W)}$$

wherein I is the current in milliamps, W is the pulse duration, and A is an intensity factor from 0% to 100% intensity. As stated, the pulse duration is generally adjustable between 50 µsec and 400 µsec. This duration is adjustable through user depression of the pulse control key 54 followed by the appropriate channel intensity keys 56. Cycle time adjustments can be made by pressing the pulse control key 54 momentarily. The pulse cycle time is typically adjustable in 0.5 second increments from 0.5 seconds to 12 seconds.

The various preferred modes available for stimulation treatment using the present invention are described below.

Normal mode: The normal mode setting defines a constant output at a selected pulse width and pulse rate to the output channels 20, 22. The user can generally adjust the pulse rate between 2 and 160 Hz, or between other selected rate values. The pulse width is generally adjustable between 50 and 400 µsec. Both output channels 20, 22 are driven with pulse waveforms that are based upon the same rate and width settings. The pulse on the second channel output 22 will be 180 degrees out of phase with that generated on the first channel output 20.

Strength duration mode: the strength duration mode is applied to the two channels 20, 22 in a modulated manner over a selectable cycle time that is variable from 0.5 to 12 seconds. During said cycle, the pulse rate is preferably fixed at 100 PPS with the nominal pulse width set at 225 µsec. A modulation range percentage from 0% to 100% is available to the patient, with this range specifying the amount of pulse width modulation deviation from the nominal width over the selected cycle time. The pulse amplitude and pulse duration are varied inversely to match the strength duration curve. At 100%, the modulation will cycle up and down the entire range of pulse duration from 50 μsec to 400 μsec. At 0%, the modulation will cease entirely since the pulse duration will be fixed at 225 μsec.

Figure 11:
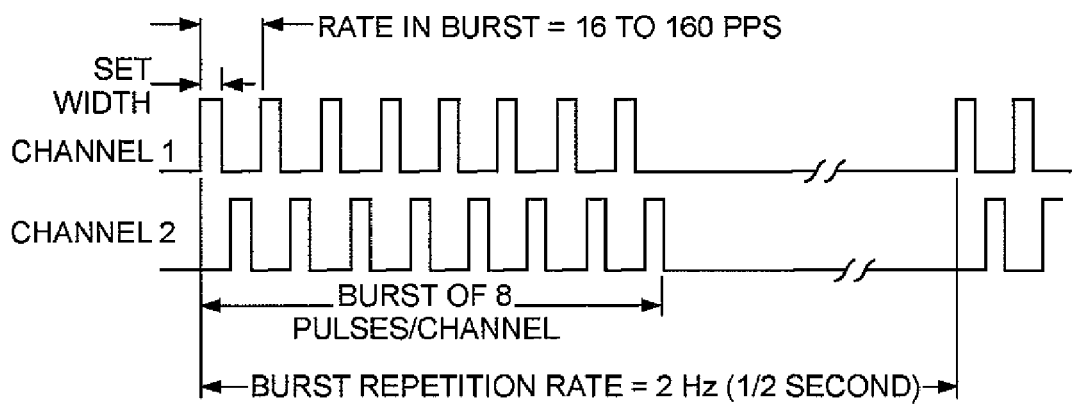
FIG. 11 is a pulse diagram representing a burst pulse output mode for a nerve stimulation device.

Burst mode: in burst mode, as shown in FIG. 11, the user selects the pulse rate over the selectable range form 16 PPS to 160 PPS during the burst, in 2 Hz increments. The output signal intensity is adjustable between 0% to 100%. Rate thresholds are imposed such that a pulse rate below 16 PPS is not permitted, and the pulse width is fixed. The repetition rate can occur at approximately a 2 Hz rate—one burst per each ½ second interval, or at other designated values/rates.

Figure 12:
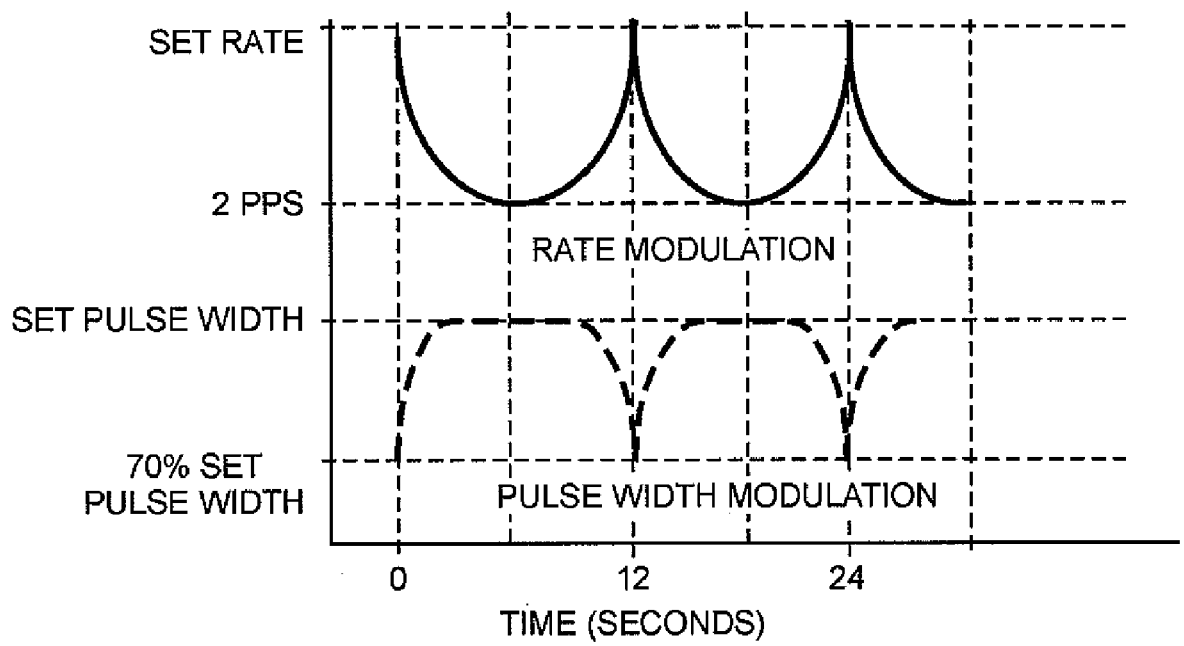
FIG. 12 is a pulse diagram representing a special modulated pulse ("SMP") output mode for a nerve stimulation device.

SMP mode: the SMP mode inversely correlates the pulse rate/cycle and the pulse duration/width modulate such that when the pulse rate increases, the pulse duration decreases. This correlation creates inverse and symmetric pulse phases for the output channels 20, 22, as demonstrated in FIG. 12. The pulse rate will generally modulate non-linearly from the set rate down to 2 PPS in a 12 second cycle, with the rate staying in the 2 PPS to 10 PPS range for ⅓ of the cycle time. Increases or decreases in this correlation are made by incrementally depressing the channel increase/decrease keys 58-64. Generally, the pulse rate range is 20 PPS to 125 PPS, and the pulse duration/width range is 50 μsec to 400 μsec.

Rate modulate mode: in rate modulate mode, the output signal is delivered with modulated pulse rates. The adjustable pulse width is constant over the normal available ranges, wherein the pulse rate modulates can be between the set rate and 66% of the set rate every 2.5 seconds, or other selected values. These values are adjustable with the corresponding keys 54, 56, with the pulse rate being selectable between 2 to 100 Hz (PPS), or other selected values.

Width modulated mode: width modulated mode controls the pulse width to alternate between the selected value and 50% of the selected value every 2.5 seconds, or other selected values. The pulse rate is selectable within the available normal range. The pulse duration is selectable between 50 μsec to 300 μsec. The pulse rate can be selectable between 2 to 125 Hz (PPS), or other selected values.

Multi-modulated mode: In the multi-modulated mode, the output is delivered with modulated pulse rate and pulse width such that both the width and rate modulate inversely to each other, and the cycle period is adjustable. The pulse width typically decreases to 50% of the set value with a 40 μsec minimum. The pulse rate when set to 100 Hz modulates to 66% of the 100 Hz, or some selected value.

Mode selection depends greatly on the particular needs and treatment goals for the user/patient. By adjusting the above-described controls and treatment variables at the input panel 14 based on prescribed treatment and/or prompting on the display panel 16, a treatment session is initiated and monitored. One important monitoring function performed by the present invention is the open lead monitoring system.

The open lead monitoring system allows the device 10 to detect an open or circuit condition at either or both of the channel outputs 20, 22. For instance, if a lead wire 110, 120 is disconnected from the channel outputs 20, 22, an open condition will be detected by the processor 74 and a preprogrammed series of steps will be initiated. At the time of detection, the processor 74 will immediately initiate an adjustment to the output channel 20, 22 such that the output signal is brought down to approximately zero. At the time of output reduction, a warning message may be displayed on the LCD screen 70. The monitoring is facilitated by a periodic polling test pulse to the channels 20, 22 such that lead continuity is monitored within 4 μsec after the generation of a pulse. If a return signal is not received, the open circuit condition is assumed. If a return signal is received, then the soft recovery function occurs.

In one embodiment, a low battery monitoring system is also in place with the device 10 during operation. With such a system, stepped indicators are processed to provide more detailed analysis of the level of battery voltage reduction that is occurring with the device 10. For instance, if three AAA (1.5 volt) batteries are being used, a total of 4.5 volts will be available at peak power. One embodiment of the present invention will monitor the voltage at the power system 24 at threshold levels of 3.2 volts, 2.7-3.2 volts, and less than 2.7 volts. While other thresholds and monitoring embodiments are obviously envisioned, these thresholds provide a good explanation of how the monitoring system works. When the battery input level reaches 3.2 volts, the unit will display a low battery indication at the LCD screen 70. When the battery voltage drops to the second threshold level of approximately 2.7 to 3.0 volts, all output will cease and the channel indicators will go off, with only the low battery indicator showing on the LCD screen 70. Preferably, at the next threshold level below approximately 2.7 volts, all power to the unit 10 will cease, including low power indications on the LCD screen 70. Obviously, other permutations on the threshold examples and monitoring are envisioned and can be implemented without deviating from the spirit and scope of the present invention. As indicated herein for other shut down sequences, the processor 74 will store parameter data (i.e., mode data, compliance data, pulse data, etc.) to the non-volatile memory 94 as part of the shut down sequence before power to the device is substantially set to zero.

Open Lead Monitoring

As further described herein for the open lead detect circuit 78 of FIG. 9c, the device 10 performs a lead continuity monitoring function that evaluates or polls the output pulse delivery, such as current, for a treatment application. It should be noted that this pulse delivery is the key monitoring event rather than mere pulse generation, which may never reach the patient due to a disruption. Treatment disruptions can include lead 110, 120 disengagement at the connectors 114, 124, poor electrode skin contact, mode changes, and the like. If such conditions are detected, the output intensity to the output channels 20, 22 is immediately set to approximately zero, or a relatively negligible current of approximately 8 milliamps or less. The levels stay at the low polling current level until the disruption is eliminated. The low polling current signal can include a single 50 μsec polling pulse, at around 5-8 milliamps, delivered to the channels 20, 22 twice a second, wherein the processor 74 monitors for a return signal. Once the disruption is eliminated, i.e., a closed lead condition is established due to the reconnection of the leads 110, 120, feedback from the polling pulse signals the processor 74, which correspondingly starts a ramp up stage which is further described herein. This disruption signal can represent no output current. When an open channel exists for either the first channel 20 or second channel 22, the processor 74 indicates the open channel condition on the display panel 16. The polling feature ensures a soft recovery that will not startle the patient when the open channel condition is corrected, and further facilitates the patient compliance monitoring system.

Compliance Monitoring

The invention accomplishes compliance monitoring by storing a number of parameters in the non-volatile memory 94 which can include EEPROM registers. As indicated, the open lead monitoring system enhances the accuracy of measuring true patient compliance. An open lead condition resulting in the low polling current levels equates to a non-compliant period. As such, accurate compliance monitoring is achieved wherein the device 10 does not count open lead periods as valid therapy periods. With such a mechanism, conditions such as disconnected electrodes and leads disrupt the output, resulting in a non-compliant open lead period. Conventional devices have monitored compliance merely according to power-on periods or output generation. With the present invention, an important distinction is made between the output generated and the output actually delivered to the patient's skin. The open lead condition monitoring makes this distinction possible as the processor 74 is continuously monitoring whether the output signal is delivered or disrupted, and when a disruption, or open lead condition, is removed.

In addition, the TENS device 10 allows for serial number storage, which can include an eight-bite serial number (ASCII characters), or other selected parameters. The serial numbers are stored within the first four locations of the memory 94. Each device 10 has a unique serial number that provides for traceability to the date of manufacture. The device 10 also includes device timer storage wherein the timers can include the patient usage timer, the device usage timer, and independent modal usage timers. The timer values will be stored within an appropriate number of locations within the memory 94.

In one embodiment, a plurality of time accumulators can be implemented to achieve compliance monitoring. First, the processor 74 software accumulates the active time during which the device 10 is delivering pulses to the patient. The time can be stored on a resolution of minutes. For instance, the accumulator can accumulate time for up to 65,000 hours which is equivalent to over seven years of operating time. The device active time accumulator is preferably stored in the non-volatile memory 94, wherein each timer can occupy three bits. The timer value can be stored once every ten minutes, or whenever the device is shutdown. The time accumulator is available to the prescribing practitioner for reading and clearing through use of the communication port 98.

The processor 74 software can also make available mode usage time accumulators that accumulate the active time in which the device 10 is delivering pulses in each of the operating modes. The times are accumulated into separate accumulators, are designed to accumulate time for up to 65,000 hours, and are preferably stored in the non-volatile memory 94 as well. Again, the timer values are stored once every ten minutes or upon shutdown of the device 10, and are available for reading and clearing through the use of the communication port 98.

A patient usage timer can be included to accumulate the active time during which the device 10 is delivering pulses irrespective of mode of operation. The time is accumulated into a time accumulator as a resolution of minutes, is preferably timed to accumulate time for up to 65,000 hours, and is also stored into the non-volatile memory 94. Again, the timer value is stored, preferably, every ten minutes and upon shut down. The patient usage timer is available for display on the LCD screen 70 and may be reset through the communication port 98.

The device 10 can also include a therapy timer. The therapy timer permits the unit to turn itself off automatically after the expiration of a programmable duration timer. This time is preferably updated/stored in the memory 94 as an operating parameter value. The duration timer is preferably programmable in steps of five minutes up to a maximum of eight hours. Other timing periods and intervals are also envisioned for use with the device 10 of the present invention. Whenever the device 10 starts delivering pulses with any amplitude approximately over 5 milliamps, the software starts a countdown using the processor 74 timing based on the setting of the therapy timer parameter. Other relatively low pulses, such as those below 8 milliamps, can be implemented as well. As such, the open lead detection/monitoring described herein affects the initiation of the actual countdown. An open lead condition will halt the countdown such that only actual pulse delivery times result in a time countdown. When the countdown timing expires, the device 10 initiates the power down sequence as the therapy duration is considered complete.

High Voltage Level Control System

As described herein, the device 10 of the present invention can provide power level indications and monitoring of low battery power at predetermined thresholds. In addition, a system of efficiently managing the consumption of power for the device 10 is also implemented. Specifically, a high voltage level control system is included which provides variable excitation of the generator control circuitry.

The high voltage level control system promotes variable control over the generator circuitry by permitting the generator to operate at a variable range controlled by the software of the processor 74 so that the output can be generated to the desired output amplitude. This prolongs battery life by avoiding running the high voltage system at the maximum level when the device 10 is operating at less than maximum output. The generator output can be variably controlled or fine-tuned by the processor 74 software. The software drives the processor 74 to preferably produce a pulse width modulated signal that varies from 0% to 100% duty cycle and correspondingly produces the desired range of high voltage level control. As a result, intelligent high voltage levels are promoted and inconsiderate operation of the generator circuitry is avoided.

The processor 74 employs the high voltage level control system of the present invention by monitoring the exact level of available voltage required at the high voltage circuit to achieve the set output level. As such, it is possible to minimize any overcharging of the high voltage circuit, and to consequently promote power conservation. The processor 74 is programmed to monitor and adjust high voltage to achieve the required output. For instance, an embodiment designed to operate with three battery sources (i.e., 3 AAA batteries), each having 1.5 volts, or a combined voltage of 4.5 volts, which provides power to the high voltage circuit, operates most efficiently when only the necessary sufficient power is provided to deliver the set output. If it is determined that 40 volts is needed, then overcharging above that level required to obtain that will be avoided, and that ideal voltage will be substantially maintained in the high voltage circuit. The processor 74 knows what the output is set at and only charges the capacitor in the high voltage circuit to the ideal level to produce that set output. For instance, the capacitor in the high voltage circuit must be set to a certain level in order for the high voltage circuit to meet the required output. The processor 74 will determine the pulses to charge the capacitor to obtain this level, and will monitor and maintain the ideal level. For example, if the set output is 50% for the high voltage circuit, there is no need to charge the capacitor to a level required to output 100% intensity. Overcharging is an innate problem with conventional devices that causes unnecessary drainage on batteries. With the present invention, when the device 10 uses a portion, or pulse, from the capacitor, the processor 74 periodically ensures that a replacement pulse(s) is directed to substantially maintain the capacitor at ideal levels.

Soft Recovery

The TENS device 10 further includes a soft recovery system designed to initiate a software routine at the processor 74 that prevents users/patients from being startled or injured when current flow at the electrodes are resumed following a treatment disruption. Treatment disruptions can include lead 110, 120 disengagement at the connectors 114, 124, poor electrode skin contact, mode changes, and the like. If such conditions are detected, the output intensity to the output channels 20, 22 is immediately set to approximately zero, or a relatively negligible current of approximately 8 milliamps or less. The levels stay at the low polling current level until the disruption is eliminated. Once the disruption is eliminated, i.e., a closed lead condition is established due to the reconnection of the leads 110, 120, feedback from the polling pulse signals the processor 74, which sets the output intensity to zero and then correspondingly starts a ramp up stage. In the ramp up stage the output intensity level is incrementally increased over a predetermined time interval to eliminate the problematic surge conditions that plague conventional units. In one embodiment, elimination of the open circuit flag at the processor 74 will cause a step up feature that permits the output amplitude at the channels 20, 22 to increase from approximately zero to the programmed or set level over a period of approximately 2.55 seconds. The low polling current signal can include a single 50 μsec polling pulse, at around 5-8 milliamps, delivered to the channels 20, 22 twice a second, wherein the processor 74 monitors for a return signal. When a return signal is detected, the described soft ramp up is performed. Preferably, the soft recovery protection is triggered when there has been a disconnection of the first lead wire 110 and/or the second lead wire 120, or when there has been a user-initiated mode change during an active treatment session. However, the mode change initiation of the soft recovery can be performed by the processor 74 software upon a change in the mode and does not require an open lead condition event. Whether this mode change is intentional or unintentional, it must be properly addressed to eliminate discomfort to the user from undesirable amplitude spikes.

Those skilled in the art will appreciate that other embodiments in addition to the ones described herein are indicated to be within the scope and breadth of the present application. Accordingly, the applicant intends to be limited only by the claims appended hereto.

The invention claimed is:

1. A method of monitoring patient compliance for implementation with an electrical nerve stimulation device, the method comprising the steps of:
   generating an output treatment signal to at least one output channel having at least one lead wire with an electrode for attachment to the skin tissue of a patient;
   monitoring at a controller the actual delivery of the generated output treatment signal to the patient by polling the at least one output channel for an open lead condition; and
   storing selected data representing patient compliance at non-volatile memory, wherein the data includes a plurality of compliance data including compliance data dependant upon sensed changes in the actual delivery of the output treatment signal to the patient.

2. The method of claim 1, further including downloading at least the compliance data at a communication port.

3. The method of claim 2, wherein the downloading of the compliance data includes downloading a patient usage timer and a device usage timer.

4. The method of claim 3, wherein the downloading of the compliance data further includes downloading a plurality of independent modality usage timers.

5. A method of using an electrical nerve stimulation device, comprising the steps of:
   inputting at least one operating parameter into the nerve stimulation device at a keypad;
   processing the at least one inputted operating parameter to generate an output pulse signal at an at least one output channel; and
   monitoring changes in the actual delivery of the generated output signal to a user through polling of the at least one output channel.

6. The method of claim 5, further comprising storing time accumulators in non-volatile memory for use in monitoring patient compliance.

7. The method of claim 6, further including downloading the time accumulators at a communication port.

8. The method of claim 7, further including uploading software to the device at a communication port, wherein the software controls, processes, and monitors operation of the device.

9. The method of claim 5, wherein monitoring changes in the delivery of the generated output signal further includes adjusting the output signal at the at least one output channel to a low level polling signal upon detection of an open lead condition.

10. The method of claim 9, further including setting the output signal to approximately zero upon detecting the removal of the open lead condition, and then gradually stepping up the output signal to substantially the level maintained prior to detection of the open lead condition.

11. The method of claim 5, further including periodically monitoring the voltage capacity of a high voltage level power system controlling output through the at least one channel, wherein an ideal voltage capacity is substantially maintained during operation to obtain the generated output pulse signal.

12. A method of monitoring a high voltage level circuit in a nerve stimulation device to conserve battery power, the method comprising the steps of:
   processing data, including inputted treatment parameters, to calculate a required electrical treatment output;
   processing the calculated electrical treatment output to further calculate an ideal voltage level needed at a high voltage circuit to obtain the required electrical output;
   generating the required electrical output for communication through at least one output channel;
   periodically monitoring the ideal voltage level at the high voltage circuit; and
   substantially maintaining the ideal voltage level at the high voltage circuit if it measurably deviates to reduce overcharging of the high voltage circuit.

13. The method of claim 12, wherein the step of substantially maintaining the ideal voltage at the high voltage circuit includes communicating pulses to the high voltage circuit to replace pulses utilized in generating the required electrical output.

14. A method of operation for an electrical nerve stimulation device, comprising the steps of:
   inputting at least one operating parameter into the nerve stimulation device;
   processing the at least one inputted operating parameter to generate an output pulse signal at an at least one output channel;
   monitoring changes in the delivery of the generated output signal to a user's skin through polling of the at least one output channel;
   initiating a low polling signal to replace the generated output signal upon detecting an open lead condition at the at least one channel; and performing a soft recovery ramp up of the output signal when the open lead condition is removed such that the low polling signal is set to approximately zero and the output signal is ramped up to a level substantially equal to the output signal generated prior to the open lead condition.

15. The method of claim 14, wherein the output signal is ramped up to a level substantially equal to the output signal generated prior to the open lead condition within a predetermined period of time.

16. The method of claim 15, wherein the predetermined period of time is some time less than 3 seconds.

* * * * *